United States Patent [19]

Strock

[11] Patent Number: 5,020,547

[45] Date of Patent: Jun. 4, 1991

[54] PROTECTIVE BODY APPLIANCE

[76] Inventor: Alvin E. Strock, 647 Commonwealth Ave., Newton Center, Mass. 02159

[21] Appl. No.: 470,858

[22] Filed: Jan. 26, 1990

[51] Int. Cl.⁵ .............................................. A61F 13/00
[52] U.S. Cl. .......................................... 128/891; 2/2
[58] Field of Search ............... 128/888, 889, 890, 891; 2/2

[56] References Cited

U.S. PATENT DOCUMENTS

| | | | |
|---|---|---|---|
| 4,000,737 | 1/1977 | Horn | 128/888 |
| 4,134,399 | 1/1979 | Halderson | 128/888 |
| 4,573,216 | 3/1986 | Wortberg | 2/2 |
| 4,641,641 | 2/1987 | Strock | 128/846 |

FOREIGN PATENT DOCUMENTS 0608770  9/1948  United Kingdom ............... 128/888

Primary Examiner—Robert A. Hafer
Assistant Examiner—Charles H. Sam
Attorney, Agent, or Firm—Cesari and McKenna

[57] ABSTRACT

A user-worn protective body appliance to prevent injury to the underlying region of the wearer's body includes a relatively rigid shield and a relatively flexible, compressible pad. The pad has a first surface to which the rigid shield is attached, and a second surface against which the body region to be protected is to be placed. The rigid shield is generally dome-shaped with such curvature as to force the relatively flexible pad, upon its attachment thereto, to assume a contour approximating that of the body region to be protected. An appropriate adhesive is applied to a limited, central portion on the second surface for securing the appliance to the body region of the wearer. In contrast, the opposite end portions on the second surface do not contain any adhesive. Consequently, when the appliance is secured to the wearer, the opposite end portions are capable of a limited degree of rocking movement in response to body movements and external forces, avoiding discomfort due to pulling of the skin at the ends of the pads and adding greatly to the comfort of the appliance, particularly during prolonged use.

20 Claims, 2 Drawing Sheets

PROTECTIVE BODY APPLIANCE

FIELD OF THE INVENTION

This invention relates generally to a user-worn appliance to protect against body injury, and more particularly to a user-worn appliance that not only can be worn for extended periods of time, but also fits against the body region to be protected in a way that maximizes comfort and minimizes inconvenience associated with its use.

BACKGROUND OF THE INVENTION

An important consideration for many individuals is protecting localized, relatively vulnerable regions of their bodies from external forces likely to be experienced in their particular environments. These individuals include the elderly, others who suffer from degenerative tissue and bone structure changes, still others who are recovering from an illness or injury that has left a region of their bodies in a vulnerable state, and athletes who because of the activity in which they engage are vulnerable to injury to a particular region of their bodies. Often, persons with pre-existing medical conditions have one or more body regions that, if subjected to external force that would not affect a reasonably healthy person, could cause serious injury to an already vulnerable part of their bodies.

Illustrative of the types of persons often in need of localized body region protection are those who, because of advanced age or past injury, are extremely prone to injury around the hip joint area. The hip joint is a ball-and-socket joint formed by the reception of the ball-shaped head of the upper part of the femur into a cup-shaped cavity in the pelvis. Particularly vulnerable is the greater trochanter which protrudes outwardly from the femur at the joint. This region is not protected by muscle of the type that surrounds the other regions of the hip. Hip joint injuries are especially common with the elderly and others who suffer from weakened bones, e.g., osteoporosis, those who suffer from neurological disorders such as Alzheimer's disease, or those who require daily medication doses which can cause them to be confused and make them susceptible to slips, tripping and falls.

Others frequently concerned about localized body region protection are those who, because of an illness or injury, are fitted with a partially or fully implanted medical device. For example, individuals with severe bone fractures often have the fractures secured by one or more implanted pins that, because of their orientation and design, extend close to or press against the inner surface of the skin. Pressure against this area even when sitting or sleeping can cause the skin to break down, resulting in ulceration. Bone securing pins of this type are commonly used in treating fractures of the hip joint.

Other partially or fully implanted medical devices requiring protection include hemodialysis connectors, medication diffusers, pacemakers, and the like. An external force directed to the region of the body in which such a medical device is fitted can disrupt the mounting of the device, causing it to malfunction or injure the skin or other body parts surrounding the device.

Certain individuals also experience considerable discomfort and pain simply when reclining or sleeping in a position which causes pressure to be applied to the body region which is to be protected. This can be particularly troublesome for paraplegics or other individuals who, due to their age or the nature of their condition, are confined to bed for extended periods of time. Such individuals are often afflicted with decubitus and other ulcers that result from prolonged body weight pressure on certain body regions and which, when left unprotected, can be extremely difficult to treat and very slow to heal.

To date, various appliances have been suggested to protect localized body portions from external forces. One such appliance is disclosed in U.S. Pat. No. 4,641,641, to the inventor of the invention of this application, for a protective appliance for the hip joint area. This appliance comprises a flexible pad adhesively secured to the wearer and a rigid shield removably secured to the pad. The shield is configured to absorb and disperse external forces to which it is exposed so as to prevent the underlying vulnerable body region from suffering their effects. This appliance is typically worn on the skin in a vertical orientation over the region of the greater trochanter of the hip joint area to protect that area against injury due to external forces.

One major limitation of many prior adhesively secured protective appliances, including the invention disclosed in the above-mentioned U.S. Patent, is that they tend to fall off the wearer with time. Simple body movements cause sections of the adhesively secured pad to be pulled away from the skin. Though the sections may re-adhere to the body in later movements, the bonding strength of the adhesive is substantially weakened. Consequently, over time, the adhesive securing the appliance becomes so weak that it can no longer hold the appliance to the body. As a result, the appliance falls off the wearer and usually has to be replaced. Pad separations of this type occur over time even with bedridden wearers whose body movements while turning in bed are relatively slight.

The short lifetimes of protective appliances resulting from repetitive pad separations of this type create various problems for their wearers. If the appliance wearer is a person suffering from a medical condition requiring long-term protection of a body region, he or she may be forced to spend considerable, possibly burdensome, sums of money frequently replacing the appliance. Furthermore, when the wearer is incapable of personally applying the appliance to his or her own skin, there are additional expenses associated with caregivers being required continually to check the wearer to verify that the appliance is in place, and when it is not, to replace it with a new one. This latter situation, and the substantial expense and inconvenience associated with it arise frequently with paraplegic, comatose and geriatric patients whose medical condition necessitates long-term wearing of the appliances.

Moreover, prior protective appliances of this type are not well suited for active individuals whose need is limited to protection for one small region of their bodies, such as the hip joint area, that normally undergoes frequent movement such as during walking and the like. Individuals wearing such appliances may find that their normal day-to-day body movements cause the appliances to separate from their bodies in short order. If such individuals do not carry replacements with them during the desired activity, they are often forced to forego protection altogether.

An improved protective body appliance, which has a much longer wear time compared to the one disclosed in the above-referenced patent, is disclosed by this inventor in U.S. patent application Ser. No. 201,170 entitled "Protective Body Appliance". This improved appliance comprises a rigid shield secured to a flexible, compressible pad which contains an outer section and an inner section. The inner section further contains two opposite end wings which are spaced away from the outer section. In use, the entire inner section is uniformly secured to the body region to be protected. The shield is thus permitted to rock back and forth to a limited degree, i.e., within the space between the inner and outer sections, while the adhesive surface of the inner section remains uniformly in contact with the skin of the wearer.

In other words, when this appliance is worn by a user, body movements and external forces which act on the rigid shield and cause it to rock one way or the other do not tend to lift the inner pad section from the skin of the wearer. The wings instead permit such rocking while the inner section remains firmly in contact with the skin. As a result, the likelihood that the adhesive bond will break is substantially reduced and the wear time of the appliance is significantly increased.

Though this improved appliance has an extended usable lifetime, it is somewhat expensive to manufacture. As noted, the pad portion of the appliance is composed of two sections, i.e., an inner section and an outer section, which are formed either by partially slicing through the ends of an one-piece pad or by securing two separate pad sections together at their centers with adhesive or the like. In addition, securing means such as snap rivets, tabs, or pockets must be provided for holding the shield relative to the pad portion. These factors add to the cost of manufacturing the appliance.

SUMMARY OF THE INVENTION

Accordingly, it is an object of the present invention to provide an improved, multi-purpose protective body appliance that covers a localized region of the body to guard against injury due to body movements or external forces.

It is another object of the present invention to provide such a protective body appliance that can be comfortably worn for extended periods of time without replacement.

It is a further object of the present invention to provide such a protective body appliance that fits snugly against the body region to be protected thereby maximizing its comfort by allowing the ends of its pad to lift away from the body in response to body movements or external forces without pulling on the skin.

It is yet another object of the present invention to provide such a protective body appliance that is relatively inexpensive to manufacture.

These and other objects will become more apparent hereinafter.

The invention accordingly comprises the features of construction, combination of elements and arrangement of parts which will be exemplified in the following detailed description, and the scope of the invention will be indicated in the claims.

Briefly, this invention includes a relatively rigid shield attached to a relatively flexible, relatively compressible pad. The rigid shield functions to protect the underlying region of the wearer's body from external forces. The pad has a first surface to which the rigid shield is attached, and a second surface which is adapted to be adhered to the body region to be protected. In the preferred embodiment, the rigid shield is generally dome-shaped with a curvature so as to force the relatively flexible pad, upon its attachment thereto, to assume a contour approximating that of the body region to be protected. As a result, the appliance can fit snugly against the vulnerable body part of the wearer. Snug fitting of the appliance solves or lessens problems such as protrusions of clothing or other inconveniences generally associated with use of similar appliances in the art.

An appropriate adhesive is applied only to a limited central portion on the second surface of the pad for securing the appliance to the skin of the wearer. The adhesive applied to the central portion of the second surface of the pad has sufficient bonding properties to secure the protective body appliance to the wearer. In contrast, the opposite end portions on the second surface do not contain any adhesive. Consequently, when the appliance is secured to the skin, these end portions are not adhered to the skin and capable of a limited degree of movement back and forth relative to the central portion of the pad, as will be explained in more detail hereinafter.

In use, the protective body appliance is secured to a selected region of the wearer's body especially prone to injury caused by external forces. The shield absorbs and deflects or disperses external forces to which it is exposed so that the underlying vulnerable body region is shielded from the same and their potentially damaging effects. In addition, the pad cushions the effect of these forces on the body.

The provision of the two non-adhesive end portions on the second surface of the pad allows for a limited degree of rocking movement of the appliance in response to the wearer's body movements and upon impact of external forces. While the central portion on the second surface of the pad remains securely adhered to the skin of the wearer, the pad ends, together with the rigid shield which is attached to the first surface of the pad, can lift away from the skin and rock back and forth relative to the body region covered by the protective appliance. Thus, when the protective body appliance experiences movements or forces that might otherwise cause wearer discomfort or pain due to pulling of the skin at the pad ends, the rigid shield and the pad of this appliance, because of the confinement of the adhesive to the central portion of the pad, move in a rocking motion while the central portion of the pad remains securely attached to the wearer. Tests show that this feature of the appliance significantly improves wearing comfort, particularly over the long-term. Additionally, because the central portion of the pad acts like a fulcrum and experiences little, if any, movement relative to the skin, the likelihood that the adhesive bond securing the appliance to the wearer will break is substantially reduced. Consequently, the adhesive bond is able to hold the protective body appliance more comfortably to the wearer for extended periods of time. A further advantage results from this appliance in that there is less adhesive area and less skin coverage, thus providing greater skin breathing and reducing the pain and discomfort associated with removal of the appliance.

Different embodiments of the protective body appliance may be provided that offer the above noted advantages as well as others. The rigid shield may be removably attached to the pad, for example, by allowing the shield to be fastened to the pad with elastic straps such as rubber bands. This allows the rigid shield to be removed from the pad for replacement with a new pad when the old pad has become soiled or poorly adhesive to the skin.

Alternatively, the rigid shield may be permanently affixed to the pad and thus constitute an integral part of the protective body appliance. Such integral construction eliminates altogether the need to provide securing means for holding the shield and the pad together.

These and numerous other advantages will be better understood and appreciated from the following detailed description of actual embodiments of the invention which are selected for purposes of illustration only and shown specifically in the accompanying drawing. In all the figures, identical numbers represent same elements.

DETAILED DESCRIPTION OF ILLUSTRATIVE EMBODIMENTS

Figure 1:
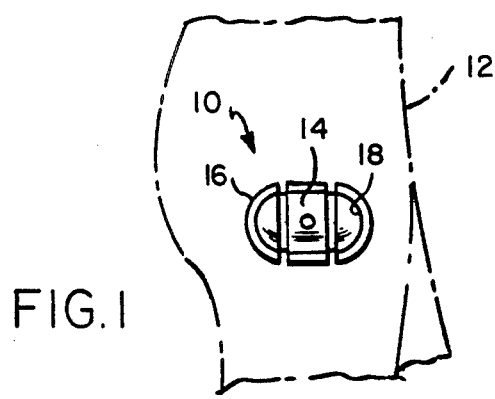
FIG. 1 illustrates a protective body appliance embodied in accordance with this invention secured to the hip joint area of a human subject depicted in broken lines.

FIG. 1 depicts a protective body appliance 10 embodied in accordance with the present invention secured over the hip joint region of a human wearer 12. The protective body appliance 10 comprises a relatively rigid shield 14 attached to a relatively flexible, relatively compressible pad 16. In the illustrated use of the protective body appliance 10, it is positioned to protect the greater trochanter of the wearer's hip joint region. The protective body appliance 10 is secured over the greater trochanter region in a generally horizontal orientation by visual and tactile location of a depression in the hip created by muscle and bone structure in this region of the body. An opening 18 formed centrally in the pad 16 aids in the proper location of the appliance 10 on the body, and in providing ventilation and breathability for the underlying skin.

Figure 2:
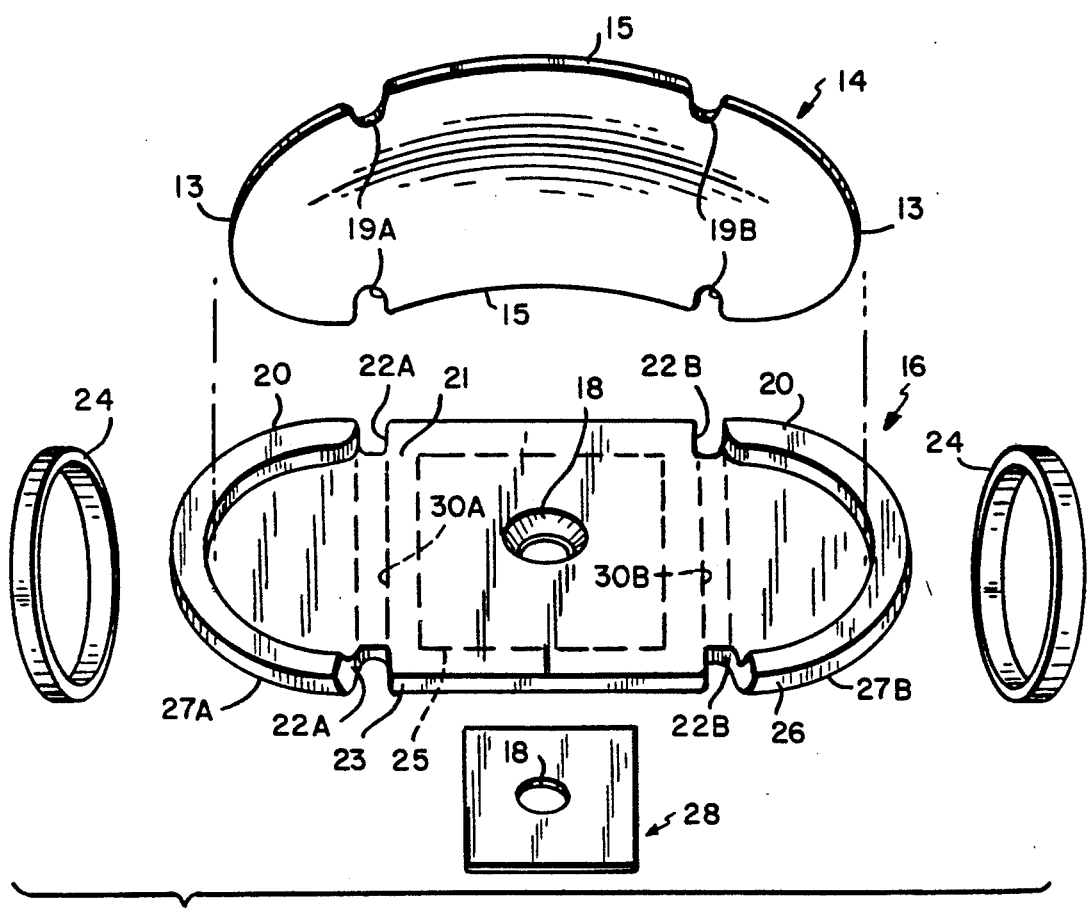
FIG. 2 is an exploded view of the FIG. 1 protective body appliance.
Figure 4:
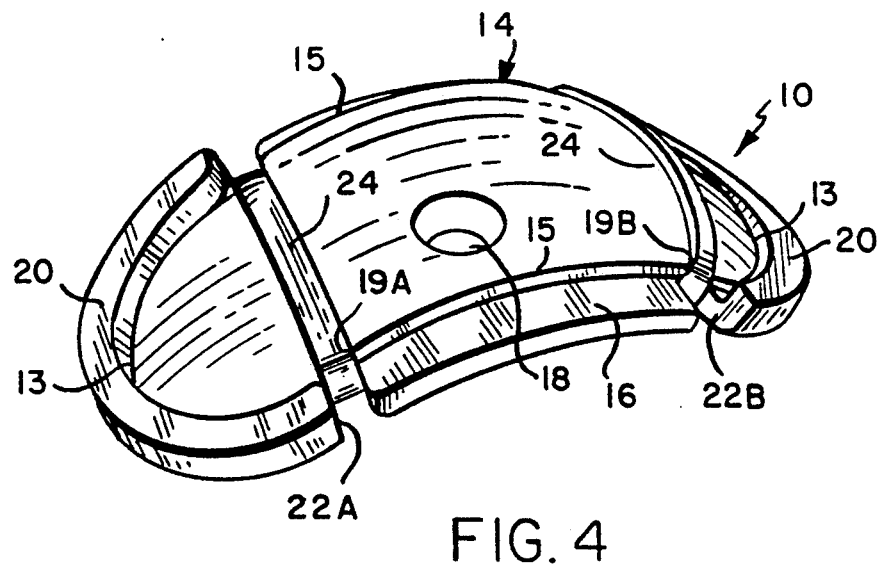
FIG. 4 is an assembled view of the FIG. 1 protective body appliance.

Referring to the exploded view of FIG. 2 and assembled view of FIG. 4, one preferred embodiment of the protective body appliance 10 is shown in greater detail. The rigid shield 14 is formed from a single piece of impact resistant material that is preferably transparent, such as the clear polycarbonate plastic marketed under the trademark LEXAN, or other suitable material. The transparency of the shield 14 provides the benefit of enabling one to visually inspect the body region which the appliance 10 overlies through the opening 18 without removing the appliance 10.

The rigid shield 14, having a generally symmetrical and longitudinal profile, has a curved shape with an approximately elliptical plan view. More specifically, the shield 14 includes a pair of arcuate edges 15 that extend along its sides from one end of the shield 14 to the opposite end thereof. In the illustrated embodiment of the invention as shown in FIGS. 2 and 4, the shield 14 subtends an area of approximately 6.5 × 13 centimeters, and has a height of approximately 4 centimeters. The shield 14 is approximately 3 millimeters in thickness.

Figure 3:
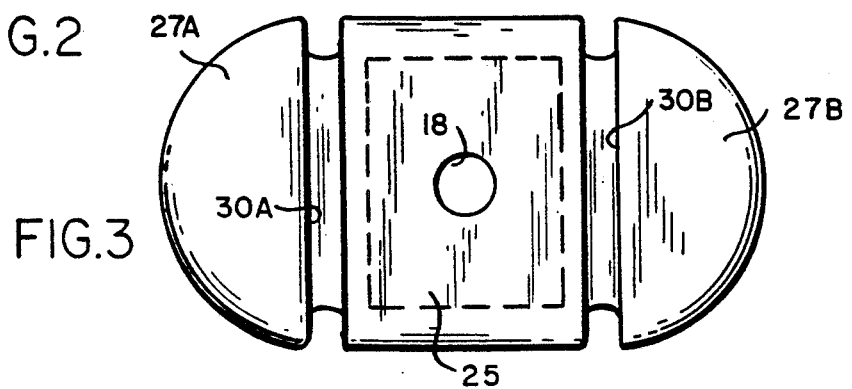
FIG. 3 is a bottom plan view of the pad component of the FIG. 1 protective body appliance.

The pad 16 is preferably made of a waterproof polyethylene foam which is inert and gentle to the skin, and may have a density of approximately 6 pounds per cubic foot. The pad 16 comprises a first surface 21 to which the rigid shield 14 is attached, and a second surface 23 which is adapted to be adhesively secured to the skin of the wearer 12 via a suitable hypo-allergenic adhesive applied to the central portion 25 thereof (defined by the dotted lines and flanked by two end portions 27A and 27B as shown in both FIGS. 2 and 3). It is preferable that the rim of the second surface 23 be bevelled inwardly in such a way as to provide a round, smooth and unobtrusive perimeter. Such bevel 26 reduces the projecting bulk of the appliance, and adds more comfort when the appliance 10 is secured to the wearer's body region to be protected. Additionally, medication may be applied to the pad adhesive so that when the protective body appliance 10 is secured to the wearer 12, the medication will diffuse into the skin of the wearer 12. A removable protective covering 28 covers and protects the adhesive prior to the protective body appliance 10 being secured in place.

The opening 18, which is formed centrally through the pad 16, is approximately 1.5 centimeter in diameter in this embodiment. However, the size and location of the opening or the number of openings may vary to suit the specific needs of the wearer 12. In appropriate cases, the openings may be used to selectively reduce the adhesive-skin contact area so as to reduce the discomfort associated with use and removal of the pad 16. It is immaterial whether an opening 18 is also formed through the protective covering 28 underlying the pad 16 as the covering 28 is removed prior to use of the appliance 10 in any event.

The pad 16 has a shape similar to the plan view of the shield 14 and is dimensioned so that it subtends an area slightly greater than that of the shield 14. In this embodiment of the invention, the pad 16 has dimensions approximately 9 × 16 × 1 centimeters. Two raised flanges 20 are provided around the rim of the opposite end portions 27A and 27B on the first surface 21 of the pad 16 to prevent the shield 14 from sliding longitudinally relative to the pad 16 after it has been releasable secured thereto. Without the flanges 20, one end 13 of the rigid shield 14 may slide away from the pad 16 and press against the skin of the wearer 12 when the shield 14 is impacted by an external force near another end 13 of the shield 14. Each of the flanges 20 has a width such that the length of the first surface 21 excluding the flanges 20 is slightly greater than that of the shield 14. In this embodiment, the width of each flange 20 is about 1 centimeter. The height of each flange 20, on the other hand, is more or less optional as long as it is sufficient to impede longitudinal sliding of the shield 14 away from the pad 16 in an assembled appliance 10. The pad 16 further includes two pairs of opposite notches 22A and 22B which are spaced apart from one another so that the adhesive-containing central portion 25 is centrally disposed in the area surrounded by the four notches 22A and 22B.

In this illustrated embodiment of the protective body appliance 10, a pair of elastic or rubber bands 24 are used to removably attach the shield 14 to the pad 16. More specifically, the shield 14 is first placed on the top of, and in alignment with, the first surface 21 of the pad 16 and then held together with the pad 16 using the bands 24. As mentioned hereinbefore, the length of the pad 16 excluding the flanges 20 is slightly greater than that of the shield 14. Thus, the shield 14 can rest on the first surface 21 of the pad 16 within the area surrounded by the flanges 20. In an assembled appliance 10, the bands 24 are engaged in the notches 22A and 22B. Such engagement prevents the bands 24 from sliding or falling off the appliance 10 thus assembled.

The bands 24 not only serve to hold the shield 14 and the pad 16 together, but also contribute to the shape or contour which the relatively flexible pad 16 is to assume in an assembled appliance 10. The contour of the pad 16 in an assembled appliance 10 is determined by several factors, i.e., the flexibility of the pad 16, the elastic strength of the bands 24, the locations of the notches 22A and 22B, and the curvature of the rigid shield 14. By proper combinations of these factors, one can always make an appliance 10 with a contour approximating that of the body region to be protected for snug and comfortable fitting. In this respect, it should be noted that the bands 24, when worn out, can easily be replaced with new ones to regain the desired contour of the pad 16 while the pad 16 is still secured to the skin of the wearer 12.

It is preferable that two shallow grooves 30A and 30B (defined by the dotted lines in FIG. 2 and more clearly shown in FIG. 3) be provided on the second surface 23 of the pad 16. These grooves 30A and 30B connect respectively each pair of notches 22A and 22B and have a depth approximating the thickness of the bands 24. Thus, the bands 24 are embedded in the grooves 30A and 30B in an assembled appliance 10. The grooves 30A and 30B, like the notches 22A and 22B, serve to prevent the bands 24 from sliding or falling off the appliance 10. Moreover, provision of such grooves 30A and 30B makes the bands 24, when in place, flush with the second surface 23 of the pad 16, thereby greatly reducing any discomfort caused by contact of the skin with the bands 24. The thickness of the pad 16 in the areas where the grooves 30A and 30B are defined is less compared with that of the remainder of the pad 16. As a result, these areas are in general more flexible. Therefore, provision of such grooves 30A and 30B also contributes to the specific contour to be assumed by the pad 16 when it is held together with the shield 14.

When the shield 14 and the pad 16 are held together by the bands 24 in the manner described above, it is desirable that the side edges 15 of the shield 14 be spaced above the pad 16 as indicated in FIG. 4. This prevents the side edges 15 from pressing into the pad 16 and against the wearer 12 when the appliance 10 is pressed toward the underlying body region due to body movements or the impact of external forces. As a result, discomfort to the wearer 12 is minimized. Further, provision of both the space between the shield 14 and the pad 16 and the opening 18 not only facilitates the evaporation of perspiration, but also makes tactile location of the body region possible when the protective body appliance 10 is in place.

As mentioned immediately above, the side edges 15 of the shield 14 are disposed above the pad 16 in the assembled appliance 10. Thus, the areas of contact of the shield 14 with the pad 16 are limited to the end edges 13 thereof. It is preferable that the end edges 13 of the shield 14 be relatively flat so as to provide a relatively unobtrusive edge for contacting the first surface 21 of the pad 16 and the flanges 20. Indeed, the shield 14 in this configuration and construction, when urged against the pad 16 by external forces, will tend not to embed therein causing impairment to the flanges 20, or worse, causing discomfort to the wearer 12.

Once the assembled appliance 10 is adhered to the wearer 12, the rigid shield 14 absorbs and deflects or disperses external forces that would otherwise impact the underlying body region. Forces that are transferred through the shield 14 to the pad 16 are dispersed through a wide body area by the opposite end edges 13 of the shield 14 which contact the pad 16. Forces transferred to the pad 16 are also attenuated due to its compressibility.

Since the opposite end portions 27A and 27B on the second surface 23 of the pad 16, unlike its central portion 25, are not secured to the skin by adhesive material, they are capable of a limited degree of rocking movement relative to the secured central portion 25 even after the assembled appliance 10 is secured to the body region to be protected. More specifically, when the end portion 27A is pressed against the soft and resilient muscle and tissue surrounding the body region to be protected upon impact of external forces, another end portion 27B is forced to move away from the skin; and vice versa. In other words, the appliance 10 functions as a lever with the central portion 25 as its fulcrum about which the lever rocks or swings. This allows the appliance 10 to shift positions in response to body movements and external forces without causing the central portion 25 to be torn away from the wearer 12.

Accordingly, when the wearer 12 is sleeping or otherwise exposing the appliance 10 to external forces, the appliance 10 itself may rock or shift position while the central portion 25 remains secured to the wearer 12. The appliance 10 thus avoids pulling of the skin at the ends of the pad and stays firmly affixed to the wearer 12 for an extended period of time, in some instances a month or more. This is a particularly important consideration in a custodial care environments where the wearer 12 requires substantially continuous protection and is often in a recumbent position and in contact with chairs, mattresses and the like.

There are significant cost savings associated with this protective body appliance 10. Since the above-described fulcrum effect functions to hold the appliance 10 to the wearer 12 for extended periods of time, the appliance 10 does not have to be replaced frequently. Also, as noted above, the shield 14 can readily be detached and reattached to a new pad 16 as the need arises. Accordingly, the cost of providing protective body appliance 10 for a wearer 12 requiring protection for a long period of time is reduced. Further cost advantages are achieved in custodial care environments because caregivers need not frequently replace protective body appliance 10 that have separated from the wearer 12.

There are other features in the embodiment of this invention shown in FIGS. 2 and 4 which further prolong the use time of the appliance 10 or add comfort to the wearer 12. For example, it is preferable that two pairs of opposite notches 19A and 19B be provided with the shield 14 which are spaced away from one another by the same spacing that exists between the pairs of notches 22A and 22B in the pad 16 and are in alignment therewith respectively when the shield 14 is properly placed on the top of the first surface 21 of the pad 16. As a result, the bands 24 are engaged in the notches 19A and 19B, as well as in the notches 22A and 22B, in an assembled appliance 10. The width of notches 19A and 19B is slightly greater than the width of the bands 24, thereby allowing some movement of the bands 24 within the notches 19A and 19B. Further, as pointed out hereinbefore, the length of the first surface 21 of the pad 16 excluding the flanges 20 is slightly greater than that of the shield 14. Thus, even when the bands 24 are engaged within the notches 19A and 19B, the shield 14 is still capable of a limited degree of movement relative to the pad 16 in response to body movements. This feature not only reduces the possibility of the pad 16 being pulled away from the skin, but also adds comfort, particularly when the wearer 12 of the protective appliance 10 reclines on it, as when sleeping or the like.

The protective body appliance 10 in accordance with the above-described embodiment of this invention may be advantageously be packaged and sold as a kit which includes two shields 14 (one for each side of the body), as well as several pads 16 and bands 24 both of which can be replaced whenever the need arises. If desired, a plurality of small dots which contain adhesive material on one of their surfaces may also be supplied in the kit. For appliances which comprise a transparent shield 14 and a pad 16 with a centrally disposed opening 18, prior placement to the center of the body region to be protected of an adhesive dot of this type with a size similar to or smaller than that of the opening 18 will greatly facilitate the securing of the appliance 10 to the desired area as visual aiming of the opening 18 at the dot is feasible. Preferably, the adhesive material used in such dots is the same as that used for the appliance 10 so that a dot can be placed on the skin of the wearer 12 for a period of time to detect, if any, allergenic reactions to the adhesive material by the wearer 12 prior to use of the appliance 10.

Figure 5:
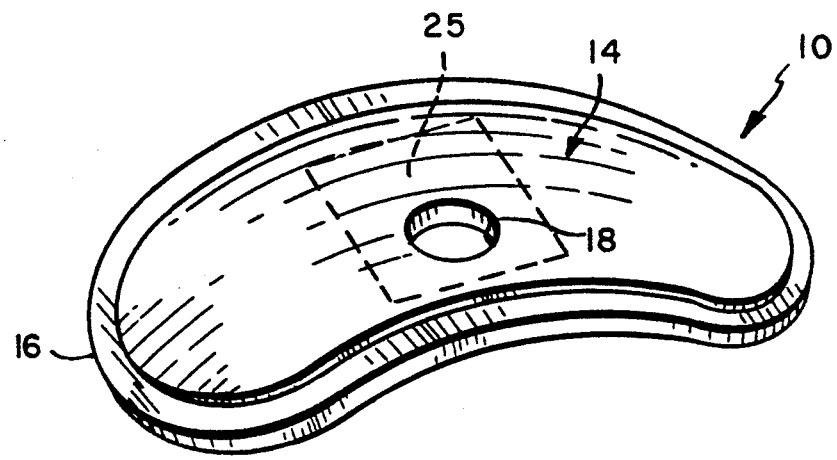
FIG. 5 is a perspective view of the protective body appliance of another embodiment.

A second embodiment of the present invention is shown in FIG. 5 where the rigid shield 14 and the pad 16 are held together permanently by suitable securing means or method, such as glue, heat fusion, or ultrasonic welding, to form an integral or one-piece protective body appliance 10. Such one-piece construction is advantaged in that it eliminates the need of providing bands or other proper securing means to the appliance. However, the whole appliance 10, including the rigid shield 14, has to be discarded when the pad 16 has become soiled, unsanitary or poorly adhesive. In the preferred embodiment for the one-piece protective body appliance 10 as shown in FIG. 5, the rigid shield 14 has a selected contour approximating that of the body region to be protected and the inner surface of the shield 14, i.e., the surface which is capable of fitting snugly against the body region, is uniformly glued to a substantial portion of the first surface 21 of the pad 16. As a result, the bond between the shield 14 and the pad 16 is maximized and separation of the shield 14 from the pad 16 is unlikely. Also, the pad 16 is thus forced to assume a contour identical or similar to that of the shield 14, to wit, one approximating that of the body region to be protected. Preferably, an opening 18 is formed at the center of the pad 16 and both the shield 14 and the means for holding the shield 14 and the pad 16, e.g., a bonding agent, are transparent so that proper position of the appliance 10 using a dot in the manner described hereinbefore is possible. Again, to yield the advantages discussed above, adhesive is applied only to a limited central region 25 of the pad surface adapted to contact the wearer's skin. This limited central region 25 is shown in FIG. 5 as a square delineated by dotted lines.

Alternatively, one can construct a one-piece protective body protector (not shown) by attaching the two end portions of the inner surface of a shield with a selected contour to a pad so that the side edges of the shield are spaced from the pad while the flexible pad is forced to assume a contour approximating that of the body region to be protected. The advantages of providing space between the shield and the pad have been discussed above in the description of the first embodiment of the present invention.

The described embodiments of the invention are preferably configured and dimensioned to cover and protect the wearer's hip joint. It is readily apparent, however, that the invention can be used to protect other body regions. For example, an individual with an implanted medication-release membrane can wear a protective body appliance of this invention to guard the membrane from physical blows that might otherwise dislodge it, or cause an excess release of medication. The protective body appliance may additionally be provided with a so-called "painless" medical adhesive, for example, of the type marketed under the trade name HYDROGEL. Such adhesives generally have good adhesion properties, but are more readily peeled from the skin when time comes for the appliance to be removed from the wearer. Such adhesives are particularly useful for athletes and the like who apply the appliance during a given athletic activity and remove it after completion of the same.

The protective body appliances of the invention also have applications for protecting surgical wounds, decubitus or diabetic ulcers, and the like. The appliances would, of course, protect the wound or ulcerated area from external forces and thus help the healing process. For this purpose, the adhesive used to secure the pad of the appliance to the skin may be a occludent adhesive, which presents a relatively benign, beeswax-like covering that promotes healing of the wound or ulcer. In this respect, a further advantage of the appliance in accordance with the first embodiment is that care of the wound or ulcer is simplified since access to the area involved is gained by simply removing the rigid shield. For this purpose, the pad of the appliance may be provided with a relatively large opening that permits visual inspection of a large area under the shield. After the wound or ulcer is inspected, the rigid shield can be reattached. This eliminates the need to remove a bandage and rebandage the wound each time access to it is required.

The foregoing description has been limited to specific embodiments of this invention. It will be apparent, however, that variations and modifications may be made to the invention, with the attainment of some or all of the advantages of the invention. Therefore, it is the object of the appended claims to cover all such variations and modifications as come within the true spirit and scope of the invention.

What is claimed is:

1. A protective body appliance to be adhered to a body region to be protected, comprising:
   a pad made of a relatively flexible and relatively compressible material having a first surface and a second surface, said second surface having a central portion which contains means for adhering said pad to the body region and having two opposite end portions which are free from said means for adhering; and,
   a relatively rigid shield having a curved shape secured to said first surface in such a manner so that said pad assumes a contour approximating that of the body region;

whereby the appliance, when adhered to the body region, is permitted a limited degree of rocking movement relative to the body region underlying said opposite end portions of said second surface and whereby said shield transfers external forces exerted upon said shield to areas spaced from said central portion.

2. The protective body appliance as described in claim 1 wherein said shield is secured to said first surface in such a manner so that a central portion of said shield is raised above said pad.

3. The protective body appliance as described in claim 1 wherein said shield is generally dome-shaped.

4. The protective body appliance as described in claim 1 wherein said means for adhering said pad to the body region comprises an adhesive substance applied to said central portion of said second surface.

5. The protective body appliance as described in claim 1 further including a covering removably secured over said central portion of said second surface to protect said means for adhering prior to use.

6. The protective body appliance as described in claim 1 wherein said shield is secured to said pad somewhat loosely permitting said shield to a limited degree of movement relative to said pad when external forces are exerted upon said shield.

7. The protective body appliance as described in claim 1 wherein said pad has a centrally disposed opening.

8. The protective body appliance as described in claim 1 wherein said shield is removably secured to said pad.

9. The protective body appliance as described in claim 8 wherein said pad includes opposite, upwardly extending flanges to prevent said shield from falling off said pad.

10. The protective body appliance as described in claim 8 wherein a pair of elastic bands are used to removably secure said shield to said pad.

11. A protective body appliance as described in claim 10 wherein said pad includes opposite, upwardly extending flanges to prevent said shield from falling off said pad.

12. The protective body appliance as described in claim 10 wherein said pad includes two pairs of opposite notches on its sides for respective engagement with each said elastic band.

13. The protective body appliance as described in claim 10 wherein said pad includes a pair of grooves extending said second surface thereof for respective partial embedment of each said elastic band.

14. The protective body appliance as described in claim 10 wherein said shield includes two pairs of opposite notches on its sides for respective engagement with each said elastic band, each not having a width slightly greater than that of each said el band as to permit said shield, while secured to said pad by said elastic bands, to a limited degree of movement relative to said pad when external forces are exerted upon said shield.

15. The protective body appliance as described in claim 1 wherein said shield is made of transparent material.

16. The protective body appliance as described in claim 1 wherein said shield is integrally secured to said first surface.

17. The protective body appliance as described in claim 16 wherein said shield is uniformly secured to said first surface.

18. The protective body appliance as described in claim 17 wherein said shield is secured to said first surface by fusion.

19. The protective body appliance as described in claim 17 wherein said shield is made of transparent material and said first surface has a centrally disposed opening.

20. The protective body appliance as described in claim 18 wherein said shield is secured to said first surface by a transparent bonding agent.

* * * * *